US007809509B2

(12) United States Patent
Milosavljevic

(10) Patent No.: US 7,809,509 B2
(45) Date of Patent: Oct. 5, 2010

(54) COMPARATIVE MAPPING AND ASSEMBLY OF NUCLEIC ACID SEQUENCES

(75) Inventor: Aleksandar Milosavljevic, Woodlands, TX (US)

(73) Assignee: IP Genesis, Inc., The Woodlands, TX (US)

( * ) Notice: Subject to any disclaimer, the term of this patent is extended or adjusted under 35 U.S.C. 154(b) by 0 days.

(21) Appl. No.: 10/140,480

(22) Filed: May 7, 2002

(65) Prior Publication Data

US 2002/0182630 A1    Dec. 5, 2002

Related U.S. Application Data

(60) Provisional application No. 60/289,497, filed on May 8, 2001.

(51) Int. Cl.
*G01N 33/48* (2006.01)
*G06G 7/58* (2006.01)
*C12Q 1/68* (2006.01)

(52) U.S. Cl. .............................. 702/19; 702/20; 703/11; 435/6

(58) Field of Classification Search ................... 702/19, 702/20
See application file for complete search history.

(56) References Cited

U.S. PATENT DOCUMENTS 5,604,100 A * 2/1997 Perlin .............................. 435/6
5,800,992 A * 9/1998 Fodor et al. .................... 435/6
6,001,562 A   12/1999 Milosavljevic

OTHER PUBLICATIONS

Pe'er et al. "Spectrum Alignment: Efaicient Resourcing by Hybridization", Proceedings of 8th Int'l Conf. on ISMB, Aug. 19, 2000, pp. 260-268. AAAI Press, Menlo Park, California.
Thomas et al. "Comparative Genome Mapping in the Sequence-Based EPA: Early Experience With Human Chromosome7", Genome Research, Mar. 21, 2000, pp. 624-633 vol. 10, CSHL Press, NY, NY.
Onyango et al. "Sequence and Comparative Analysis of the Mouse 1-Megabase Region Orthologous to the Human 11p15 Imprinted Pomhin" Genghb. Res., Sep. 19, 2000, pp. 1697-1710 vol. 10, CSHL Press, NY, NY.
Kuehl et al. "An Effective Approach for Analyzing Prefinished Genomic Sequence Data" Genome Res. Dec. 10, 1998, pp. 189-199 vol. 10, CSHL Press, NY, NY.
EX Huang et al. "CAP3: A DNA Sequence Assembly Program," Genome Res., Jul. 14, 1999, pp. 868-877. vol. 9, CSHL Press, NY, NY.
Schwartz et al. "Pipmaker-A Web Server for Aligning Two Genomic DNA Sequences" Genome Res., Feb. 1, 2000, PP. 577-586, vol. 10, CSHL Press, NY, NY.
Bovck et al. "Analysis and Quality and Utility of Random Shotgun Sequencing at Low Redundancies" Genome Res., pp. 1074-1084, Sep. 18, 1998, vol. 8, CSHL Press, NY, NY.
Delcher et al. "Alignment of Whole Genomes", Nucleic Acids Res., Apr. 14, 1999, pp. 2369-2376., vol. 27 No. 11, Oxford Univ. Press, Oxford, England.
Florea et al. "Web-Based Visualization Tools for Bacterial Genome Alignments" Nucleic Acids Res., Jul. 27, 2000, pp. 3486-3496, vol. 28, No. 18, Oxford Univ. Press, England.
Myers et al, "A Whole-Genome Assembly of Drosophila", Science Magazine, Mar. 24, 2000, pp. 2196-2204, vol. 287, Am. Assoc. for Advancement of Science, Washington, DC.
International Human Genome Sequencing Consortium "Initial Sequencing and Analysis of the Human Genome", Nature, Feb. 15, 2001, pp. 860-921, vol. 409, MacMillan Publ. Ltd, New York, New York.

* cited by examiner

*Primary Examiner*—Shubo (Joe) Zhou
(74) *Attorney, Agent, or Firm*—Aleksandar Milosavljevic

(57) ABSTRACT

A method for assembling nucleic acid sequence fragments is disclosed. The fragments are assembled using information about their relative position inferred by comparison of the fragments against a known sequence of a related nucleic acid (FIG. 3). Additionally, the method localizes fragments to bacterial artificial chromosomes (FIG. 1) and determines relative position of bacterial artificial chromosomes using sequence comparison information (FIG. 6). The method utilizes the information about relative orientation, mutual distance, fragment localization to bacterial artificial chromosomes, and relative position of bacterial artificial chromosomes to constrain the assembly process (FIG. 5), thus resulting in a more accurate assembly requiring fewer sequencing reactions.

9 Claims, 2 Drawing Sheets

Aleksandar Milosavljevic

COMPARATIVE MAPPING AND ASSEMBLY OF NUCLEIC ACID SEQUENCES

CROSS-REFERENCE TO RELATED APPLICATIONS

Figure 1:
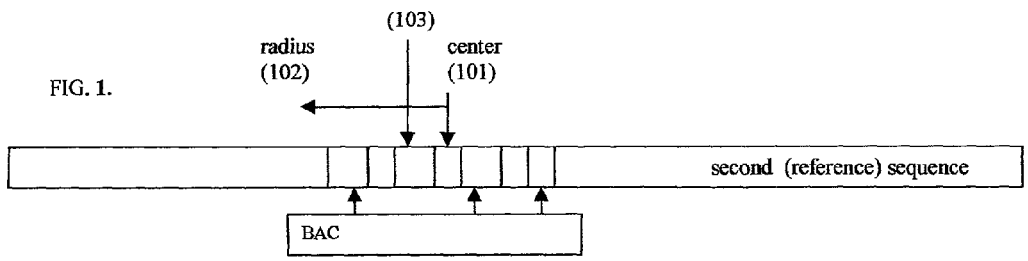

This application claims benefit of priority to U.S. Provisional Patent Application Ser. No. 60/289,497, filed May 8, 2001, the entire contents of which are incorporated herein by reference.

FIELD OF THE INVENTION

The invention relates to methods of determining nucleic acid sequence and of detecting similarities between known and unknown nucleic acids. In a particular embodiment, the invention concerns methods for determining nucleic acid sequence of fragments from first nucleic acid using dideoxy sequencing and comparison of the fragments of first nucleic acid against the sequence or a sequence scaffold of second nucleic acid.

BACKGROUND OF THE INVENTION

Determination of sequence of DNA and other nucleic acids is currently mostly performed through the classical dideoxy sequencing method. Dideoxy sequencing reactions provide readouts of short (100-900 bp) sequence fragments per experiment (ref. 20,21).

If the sequence of the original nucleic acid that is targeted for sequencing is longer than the relatively short readout length of dideoxy sequencing reactions, a "shotgun" method is employed. In the first step of the shotgun method, the original nucleic acid is chemically broken in a random fashion into a set of fragments of shorter length. In practice, a large number of original identical nucleic acid molecules is broken simultaneously and independently in the course of a single chemical reaction, thus resulting in a multitude of overlapping fragments. In the second step of the shotgun method, a number of individual fragments are sampled by well established methods, sequenced and assembled, revealing the sequence of the original nucleic acid (ref. 20,21).

The assembly of sequenced fragments proceeds in a domino-like fashion. Sequence similarity between the end of one fragment and the beginning of subsequent fragment guides the assembly process. Fragment assembly is recognized as a major bottleneck in many ongoing large-scale DNA sequencing efforts (ref 20,21).

Most currently available programs for sequence assembly such as Phrap, CAP3, TIGR, and Celera assembler use the classical "Overlap-Layout-Consensus" ("OLC") fragment assembly method (ref 1, 3, 5, 13, 16, 24). The main problem occurs in the "overlap" step: the overlap comparisons typically result in a large number of either spurious matches or undetected matches between fragments due to the uneven coverage of the target sequence, short overlaps between fragments, dideoxy sequencing errors, and, most importantly, due to the presence of repetitive elements.

To see how the presence of repetitive elements causes an assembly problem, consider a situation where the sequence at the end of one fragment matches the sequence at the beginning of another fragment. This situation may arise either due to the fact that the two fragments overlap in the original sequence or due to the fact that each fragment overlaps with a distinct occurrence of the same repeated sequence but the fragments themselves do not overlap in the original sequence. In the former case, the fragments should be assembled together, while in the latter they should not. The problem is that the currently available methods do not correctly discriminate between the two situations. Thus, a large number of erroneous overlaps induced by the presence of repeats results in an erroneous assembly. The problem is further exacerbated by other factors such as low redundancy of coverage of the region of interest by sequence fragments, uneven coverage by fragments, chimerism of fragments, contamination of fragments by vector and other foreign DNA sequence, and the presence of dideoxy sequencing error.

A number of methods are used in practice in order to reduce the problem posed by the presence of repetitive elements: (1) databases containing sequences of repetitive elements are used to screen repeat-containing fragments prior to the "overlap" stage, thus preventing erroneous assembly due to known repeats (ref. 20,21); (2) repeat-induced false overlaps between fragments are partially eliminated in the "layout" step of the OLC method by heuristic procedures (ref. 16); (3) specialized repeat-finding methods are developed to recognize repeats in the overlap stage of the OLC method and then feed the information about repeat-induced overlaps back to the assembly method (ref. 17); (4) repeat finding is accomplished through detection of "tangle" structures in the Eulerian Path assembly method (ref. 19).

None of the methods have been very successful in dealing with repeats on a large-scale. In fact, it has been recognized that the problem posed by repetitive DNA cannot even in principle be solved by methods that assemble fragments shorter than the length of the longest repeated sequence (ref. 19). Thus, a need has been recognized to obtain and utilize higher-level information about relative positions of sequence fragments in order to enable correct sequence assembly (ref 20,21).

One approach to solving the assembly problem is the so-called double-barrelled DNA sequencing method (ref 22, 12, 15). The method uses the information about approximate distances of fragments that are sequenced from opposing ends of a clone insert of known approximate size. Such fragments have been referred to as "mate pairs". The distances between mate pairs have been applied in the framework of the same OLC method and have lead to some improvement (ref. 8).

While it provides useful information and helps bridge repeat-induced gaps in the assembly process, the double-barrelled method has a number of disadvantages. First, it is more costly to sequence and correctly track mate pairs than individual random fragments. In order to obtain the distance between mate pairs, clone sizes may need to be measured and controlled. Many clones may be sequenced from one end only, thus resulting in mispaired fragments. Chimeric fragments often result in mispaired mates, thus introducing error in the assembly process.

While the double-barrelled DNA method can recognize and eliminate a fraction of repeat-induced overlaps, it cannot help completely close the gaps in the assembly of repeat-rich regions. However, the information about the distances between mate pairs can at least indicate the approximate size of gaps between assembled "islands", thus guiding further "gap filling" efforts.

Instead of producing a completely assembled sequence, the double-barrelled DNA sequencing results in a "scaffold" (ref 18), which is defined as a partially assembled sequence consisting of numerous assembled islands that are separated by gaps of known size. The recently published initial draft of human genome sequence is in fact a scaffold consisting of a huge number of assembled islands (ref 21).

Second approach to solving the assembly problem is the so-called "hierarchical.shotgun sequencing" (ref 20), also referred to as "map-based", "BAC-based", or "clone-by-clone". This approach involves generating and organizing a set of large-insert clones (typically 100-200 kb each) covering the target nucleic acid and separately performing shotgun sequencing on appropriately chosen clones. The reasoning behind the method is that, because the sequence information is local, the issue of long-range misassembly is eliminated and the risk of short-range misassembly is reduced.

One problem with the hierarchical shotgun approach is that the shotgun step needs to be repeated for every clone. In order to sequence the genome of a human or a rodent, tens of thousands of clones need to be subjected to the shotgun step. A shotgun at the level of the whole genome is less costly and easier from an operational point of view.

The double-barrell and hierarchical shotgun approaches have been combined in practice. As part of the human genome sequencing effort (ref. 20,21), certain number of fragments are obtained by performing shotgun sequencing of individual clones, another number of fragments are obtained by performing shotgun sequencing at the level of the complete original nucleic acid (e.g., whole genome), and some of the fragments from either set are mate pairs.

The two methods for producing fragment assembly (ref 16,24) that were used in the actual assembly of the initial draft sequence of the human genome (ref. 20,21) implement the OLC method. They utilize the following pieces of information in the assembly process: (1) sequences of fragments of nucleic acids (for example, sequences of fragments obtained by the shotgun method); (2) sequences of repetitive elements that were identified prior to the current assembly (in order to avoid false fragment overlaps in the layout stage); (3) information about false fragment overlaps (for example, about those overlaps induced by the presence of as yet unknown repetitive elements); (4) information about the approximate distance between pairs of fragments (for example, the distance between mate-pairs resulting from the sequencing of the ends of clones of known size as part of the double-barrell shotgun method); (5) information about localization of fragments within the same subregion (for example, within the same BAC clone in case of human genome sequencing); and (6) information about overlaps and the relative order of subregions (for example, overlaps and relative order of BACs).

In addition, to the classical OLC method, Indury and Waterman (ref 6) and Pevzner (ref 19) proposed the Eulerian Path method for sequence assembly. Eulerian Path method is based on the ideas that came from the method of Sequencing By Hybridization ("SBH"), as outlined in U.S. Pat. No. 5,202, 231. On one hand, SBH problem is computationally similar to the problem of dideoxy fragment assembly. On the other hand, the SBH fragments are obtained by probe-specific hybridization and are thus much shorter (typically 5-30 bp long) then the fragments obtained by dideoxy sequencing (typically 100-900 bp long) (ref. 10).

The similarity between the two fragment assembly problems is such that OLC method was also initially used in an attempt solve the SBH problem (ref 2, 7). The OLC problem did not scale up computationally. In 1989, Pevzner (ref. 11) proposed the Eulerian Path method for the SBH problem which overcame the scaleup problem, at least in the ideal case of error-free data.

Indury and Waterman (ref 6) applied the Eulerian Path method to the problem of assembling longer fragments obtained by dideoxy sequencing. The first step in the Indury-Waterman method is to break the fragments into yet smaller overlapping subfragments and then, in the second step, to assemble the subfragments by applying the Eulerian Path method proposed by Pevzner. Unfortunately, the Idury-Waterman approach did not scale up well due to sequencing error that occurs in practical dideoxy sequencing. An error-correction step and repeat-detection step have recently be proposed that significantly improve performance of the Euler Path method (ref. 19). Despite the improvements, the Eulerian path method still cannot accommodate information about fragment distances (for example, mate pair information) and cannot calculate scaffolds, and thus it still cannot compete with other assemblers (ref 16, 24) in the assembly of genomes of higher organisms. Nevertheless, the method appears to perform well on the assembly of small genomes (for example, bacterial genomes around 2 mb in size) when the redundancy of fragment coverage is high.

Significantly, none of the assembly methods discussed above utilize the information about known sequences of different but similar nucleic acids. On the other hand, U.S. Pat. No. 6,001,562 discloses a method where sequence similarity between two nucleic acids is determined by aligning fragments from one nucleic acid against the second nucleic acid. However, U.S. Pat. No. 6,001,562 does not teach the method of using the relative position information between distant fragments; nor does it teach the method of inferring repetitive subsequences; nor does it teach localizing fragments to specific cloned DNA fragments; nor the method of inferring relative position of cloned fragments, as described in the present invention.

It follows from the foregoing that none of the prior art references teaches means of using a known sequence of a nucleic acid to drive the assembly of the sequence of another related nucleic acid by inferring distance and orientation of subsequences of the related nucleic acid, with only partial exception of U.S. Pat. No. 6,001,562, which teaches the method for using such information when the subsequences overlap. However, U.S. Pat. No. 6,001,562 does not teach the method for using such information when the subsequences do not overlap but instead occur at a distance from each other Thus, even U.S. Pat. No. 6,001,562 teaches a method of utilizing only a small fraction of the information that is useful in overcoming the critical problem of sequence assembly in the presence of repetitive nucleic acid sequences.

SUMMARY OF THE INVENTION

In addressing the limitations in the prior art, the present invention provides a comparison-based method for assembly of the sequence of a nucleic acid that overcomes the limitations of the prior art. The proposed method considers information about sequence fragments and the information about their relative position that comes from both the chemical experiments on one hand and that is inferred from the comparison of sequences of fragments of the nucleic acid against the sequences or scaffolds of other nucleic acids on the other hand.

Thus, in accordance with the present invention, there is provided a method for inferring relative position of occurrence in the first nucleic acid of at least two sequence fragments derived from the first nucleic acid by performing sequence comparison of said sequence fragments against at least the second nucleic acid and by further processing the result of the comparison in order to infer the relative position of the two fragments.

In one embodiment of the method the sequence fragments are determined by dideoxy sequencing. In another embodiment of the method the sequence fragments are determined by the shotgun method. In yet another embodiment of the method at least one of the two sequence fragments overlaps a third sequence fragment, thus allowing inference of relative positions of the three fragments. In yet another further embodiment of the method at least one of the two sequence fragments is a mate pair of a third sequence fragment, thus allowing inference of relative positions of the three fragments. In an even yet another embodiment of the method the two sequence fragments belong to two distinct clones, thus allowing relative positioning of the clones.

If complete sequence of second nucleic acid is available, then it is appropriate to use the complete sequence in the comparison. Otherwise, partial sequence of the second nucleic acid is used in the comparison. If available, a scaffold or a set of scaffolds of the second nucleic acid is used in the comparison.

The second nucleic acid is similar to the first nucleic acid. Such is the case when the first and second nucleic acid are derived from distinct but related species. In another embodiment, the second nucleic acid and the first nucleic acid are derived from different organisms from the same species. In even yet another embodiment of the method, the second nucleic acid and the fragments are derived from distinct mRNA transcripts. In still another embodiment, the second nucleic acid is genomic DNA and the fragments are derived from a mRNA transcript. In a still yet another embodiment of the method the second nucleic acid is derived from a mRNA transcript and the fragments are derived from genomic DNA. In a further embodiment of the method the second nucleic acid consists of a plurality of molecules, each such molecule being partially or fully sequenced.

In another embodiment, a plurality of second nucleic acids is used instead of a single nucleic acid, and the information about relative positions of the two fragments is obtained by combined processing of the information obtained from comparisons against individual nucleic acids in order to improve accuracy or completeness or both of the information about the inferred relative positions.

In addition to the length of distance, the inferred relative position information further possibly comprises at least one of the following: an indicator of accuracy of the inferred relative position; an indicator of precision of the relative position; an indicator of the probability of the inferred relative position; an indicator of confidence of the inferred relative position; confidence bounds for the inferred relative position.

In a yet another embodiment, the method for inferring relative positions comprises one or more adjustable parameters that affect the inferred relative position information. In a further embodiment of the invention the adjustable parameters are selected based on a control set of fragments of known relative positions and based on a criterion that comprises a measure of agreement of inferred relative positions under certain parameter settings on one side with relative positions of the fragments that are determined by a second independent method or by the same method but under different parameter settings on the other side.

In yet another embodiment of the method, the relative position information is whether or not the two fragments both occur within the same subregion of the first nucleic acid. In a further embodiment the subregion is a clone contained in Bacterial Artificial Chromosome clone ("BAC"). In a still further embodiment the size of the subregion is between 5 kb and 100 Mb.

In a further embodiment of the method, the information about the relative position of one or more fragments is further used to detect overlap between two subregions of the first nucleic acid. In a further embodiment of the method the subregion is a clone contained in Bacterial Artificial Chromosome clone ("BAC"). In a still further embodiment the size of the subregion is between 2 kb and 100 Mb. In a yet further embodiment of the method the overlap of two subregions is detected by detecting a region within the second nucleic acid where fragments derived from the two subregions match in an interleaved fashion.

In a still another embodiment of the method, the inferred relative position information is distance between the two fragments. In an embodiment of the foregoing the distance is between 2 kb and 100 Mb. In a still another embodiment of the invention, the distance information further comprises at least one of the following: an indicator of accuracy of the inferred distance; an indicator of precision of the inferred distance; an indicator of the probability of the inferred distance; an indicator of confidence of the inferred distance; confidence bounds; probability distribution over distances; a histogram of distances.

In a further embodiment of the method of inferring distance between the two fragments, further step of discovering novel repetitive sequence that induces end-sequence similarity between fragments that are inferred to map at a distance despite the end-sequences of the two fragments.

The method further comprises the step of using the inferred relative positions of the fragments in the assembly of the sequence of first nucleic acid. In an embodiment of the foregoing, the assembly step is performed using the commonly used PHRAP method (ref. 20). The assembly step is performed using the Staden method (ref 1), CAP3 method (ref. 5), TIGR assembler method (ref. 13), Greedy Path-Merging method (ref 16), EULER method (ref. 19), Whole Genome Assembly method (ref. 8,21) GigAssembler method (ref. 20,24), or any other related method selected as described in the detailed description.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and the scope of the invention will become apparent to those skilled in the art from this detailed description.

FIGURES

The following drawings form part of the present specification and are included to further demonstrate certain aspects of the present invention. The invention may be better understood by reference to one or more of these drawings in combination with the detailed description of specific embodiments presented herein:

FIG. 1: Inferring localization of fragments within a subregion of a nucleic acid. Center of subregion (101) is a position in the reference nucleic acid. The center is obtained by averaging positions where fragments that are known to fall within the subregion in the original nucleic acid match reference nucleic acid. Radius (102) is one half the estimated size of the subregion from the original nucleic acid. If a fragment (103) from the first nucleic acid of unknown localization matches reference sequence within the Radius of the Center of subregion, it is inferred that it also falls within the subregion of the original nucleic acid.

Figure 2:
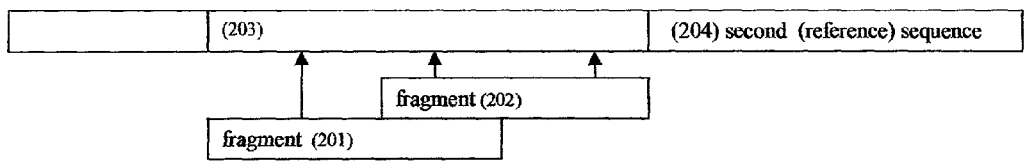

FIG. 2: Inferring an overlap of fragments. An overlap of two fragments (201 and 202) from the original nucleic acid is inferred if they match in an overlapping fashion a region (203) in the reference nucleic acid (204). Two fragments whose overlap is inferred at high confidence may be replaced by a single fragment that results from the assembly of the two fragments.

Figure 3:
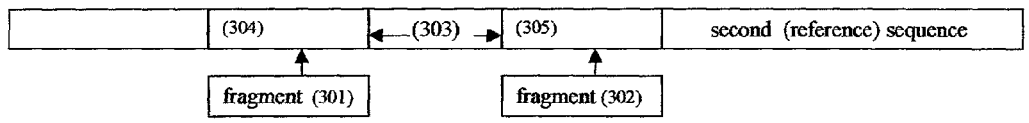

FIG. 3: Inferring distance between fragments. Inferred distance between two fragments (301 and 302) from the original nucleic acid is inferred as the distance (303) between unique strong matches (304 and 305) of the two fragments in the reference sequence.

Figure 4:
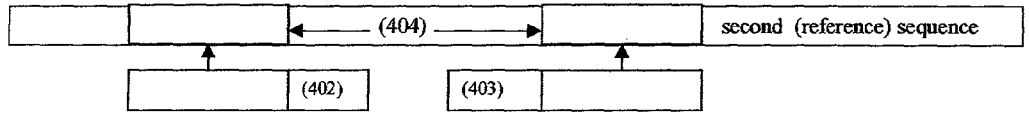

FIG. 4: Breaking an overlap induced by repeat sequence. If the end sequence (403) of one fragment from the original nucleic acid (401) matches the beginning sequence (402) of the other fragment but the fragments are inferred to occur at a distance by comparison against the reference nucleic acid, presence of repetitive element is inferred. A situation is illustrated where the repetitive element occurs twice in the reference sequence. Notice that the repetitive sequence itself is detected by this method. The newly detected repetitive sequence is in turn used to screen for and eliminate other repeat-induced overlaps.

Figure 5:
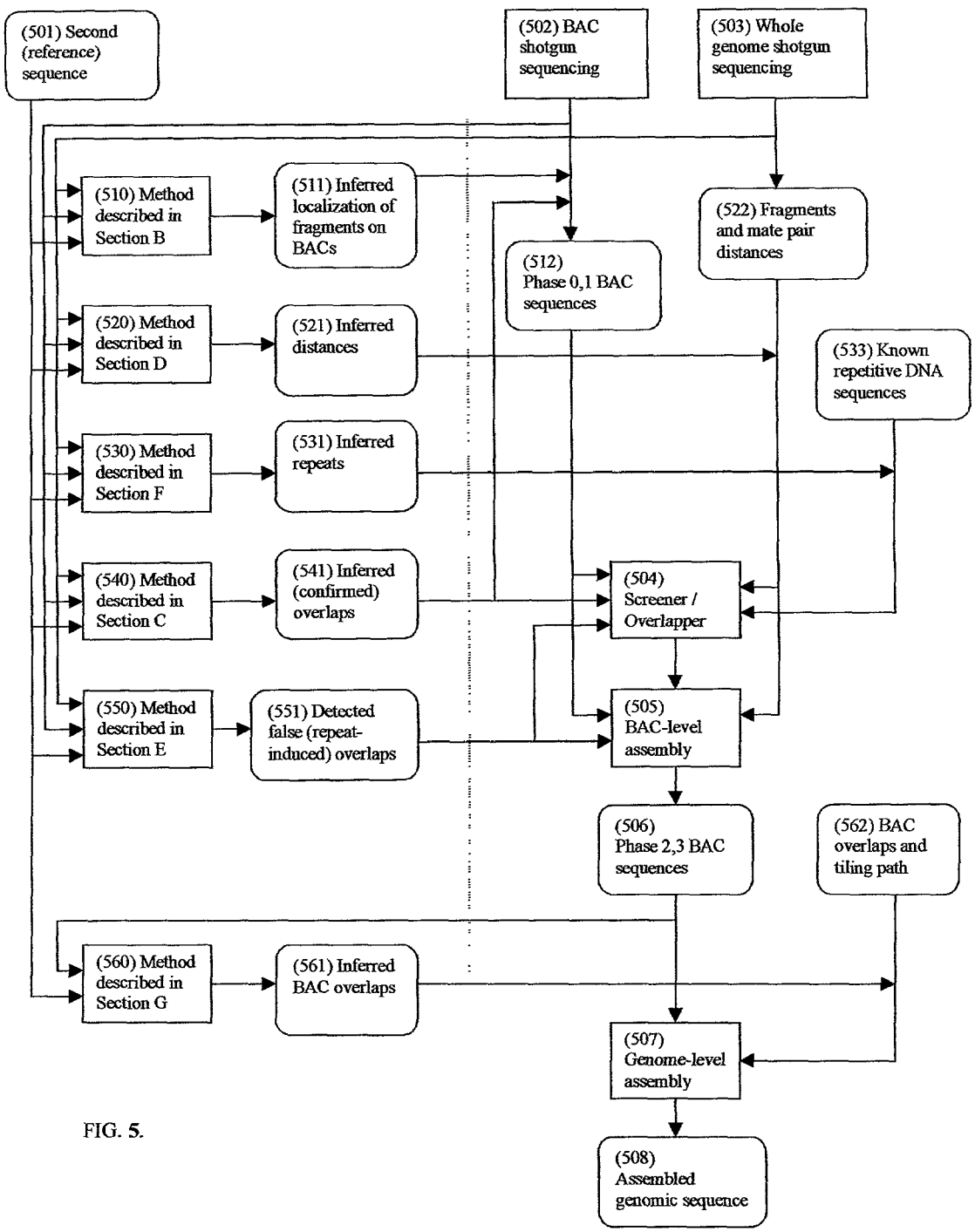

FIG. 5: This block diagram describes the information flow in the disclosed method. The portion of the diagram to the left of the dotted line illustrates the methods of inferring positional information based on reference sequence (501). The six grayed blocks correspond to the six methods for inferring positional information disclosed in sections B (block 510), C (540), D (520), E (550), F (530), and G (560). Localization information (511) is inferred (510) as described in section B and the newly localized fragments are simply added to the appropriate BACs (512) for processing by the screener/overlapper (504) and the BAC-level assembler (505). Distance information (521) is inferred (520) as described in section D and the newly inferred fragment distances are simply added to the appropriate mate pair distance information (522) for processing by the screener/ overlapper (504) and the BAC-level assembler (505). The information about new repeats (531) is inferred (530) as described in section F and the newly inferred repeat sequences are simply added to the database of known repeat sequences (533) for processing by the screener/overlapper (504). The information about confirmed overlaps (541) is inferred (540) as described in section C and made available for use by the screener/overlapper (504), and the confirmed overlaps that come from a particular BAC are used to assemble the shorter fragments into a longer fragment and thus increase the phase (from 0 to 1) of individual BACs (512). The information about repeat-induced overlaps (551) is inferred (550) as described in section E and made available for use by the screener/overlapper (504) and the BAC-level assembler (505). The information about subregion (BAC) overlaps (561) is inferred (560) as described in section G, is simply combined with the overlap information obtained by physical mapping (562), and then made available for use by the genome-level assembler (507).

Figure 6:
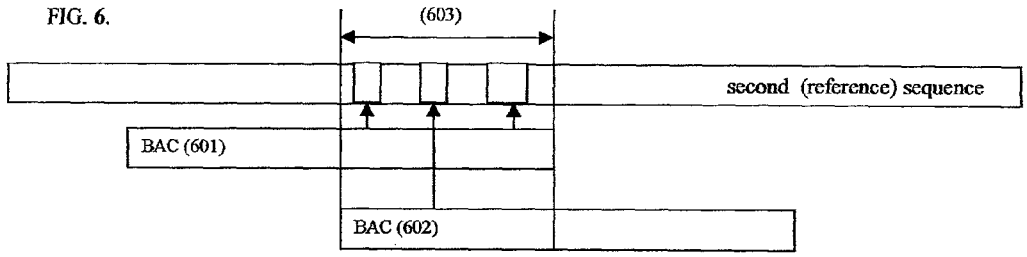

FIG. 6: Inferring an overlap of subregions from first nucleic acid. An overlap of two subregions (601 and 602) from the original nucleic acid is inferred if sequence fragments derived from both subregions match in an interleaved or overlapping fashion a region (603) in the reference nucleic acid (604). Two subregions whose overlap is inferred at high confidence may be replaced by a single subregion that results from the assembly of the two subregions.

DETAILED DESCRIPTION OF THE INVENTION

The term "genome deciphering" has often been used to summarize newly completed DNA sequencing projects. However, the true deciphering will require the development of an understanding of the function of DNA sequence, an effort that will take decades. To decipher biological function of DNA sequence, a number of approaches are currently pursued. The most powerful of them involves yet more DNA comparative sequencing of related species (ref. 25):

"Probably the most powerful tool to identify the coding exons, as well as the regulatory regions, is a comparison of the sequence across different genomes For that purpose, full-scale sequencing of the laboratory mouse genome already has been initiated, and the sequencing of the rat and zebrafish genomes will not be far behind. In both the public and private sectors, serious consideration is being given to the sequencing of other large vertebrate genomes, including the pig, dog, cow, and chimpanzee . . . ."

The more similar the reference nucleic acid sequence to the sequence of the original nucleic acid, the more effective will be the method disclosed in the present invention compared to the classical OLC process. As the number of sequenced genomes increases, the utility of the disclosed method will rapidly increase. In particular, because the similarity of genomic sequences of primates exceeds 90%, the assembly of the genomes of chimpanzees and other primates will be greatly improved through the use of the human reference sequence. Even genomes of not so closely related species such as humans and mice share an average 85% similarity in biologically important protein coding exon regions (ref 20), thus opening the opportunity to save considerable effort in the sequencing of these important regions in mice by applying the disclosed method. Another obvious immediate utility of the method is in the sequencing of genomes of different organisms within the same species where the reference genome sequence for the species is already known. Genomic sequence similarity across different organisms within a species, such as humans, typically exceeds 99%. The classical OLC method for sequence assembly (ref 16,20,21,24) utilizes the following pieces of information in the assembly process: (1) sequences of fragments of nucleic acids; (2) sequences of known repetitive elements; (3) information about false fragment overlaps; (4) information about the approximate distance between pairs of fragments; (5) information about localization of fragments within the same subregion (BAC); and (6) information about the relative position and overlaps between subregions (BACs).

It is important to note that the source of all the information utilized by the classical OLC method and listed above is the original nucleic acid sequence. In contrast, the disclosed method augments or completely replaces the need for this information by employing the information obtained by comparisons of fragment sequences against another known reference sequence or a scaffold.

The present method assumes that a number of fragments are obtained from the first nucleic acid. Second (reference) nucleic acid, or a set of other nucleic acids are then identified that satisfy the following two criteria: (1) sequence fragments, complete sequence or sequence scaffolds from the second nucleic acid are available and (2) it can be reasonably assumed that there is similarity between the sequences of the first and second nucleic acids.

A. Calibration Methods

Prior to inferring positional information, calibration of the method needs to be performed by setting the threshold T. The threshold is used to estimate whether or not a fragment from the first nucleic acid has an orthologous match in the second nucleic acid: if the match exceeds T, the match is declared to be orthologous, if the match falls below T, it is declared non-orthologous.

In order to set the threshold, the degree of similarity between the first and second nucleic acid is first estimated. The degree of similarity is measured by aligning known orthologous sequences from the two nucleic acids. If the exact orthologs are not known, long stretches of genomic DNA may be used as surrogates. The comparisons should yield the information about the expected percent similarity between orthologous regions.

The information about the percent similarity between orthologous regions is then used to set threshold T of percent similarity so that most (preferably 85%) orthologous matches fall above the threshold.

It should be noted that the threshold T may be based either on the comparison of nucleic acid sequences or on the comparison of inferred amino acid sequences, where appropriate. Typically, one threshold would be appropriate for amino acid coding regions while another threshold would be appropriate for other regions.

Once the threshold is initially determined, it is further adjusted for accuracy of positional information. For that purpose, a set of mate pairs needs to be used. The mate pairs are compared against the second nucleic acid in order to identify matching mate pairs. A mate pair identified as matching the second nucleic acid sequence if both of the mates match the second nucleic acid above threshold T.

Next, the distances between the matches in the second nucleic acid ("inferred distances") are compared against the expected mate pair distances ("measured distances"). Since the measured distances are known only to a certain degree of accuracy (ref 16), a mate pair distance is considered to be correctly inferred if it falls within three standard deviations from the measured distance. Threshold T is then further adjusted so that most (preferably 80%) of distances are correctly inferred.

In addition to calibrating the threshold T, the comparison of inferred and measured distances is used to estimate the confidence interval for the inferred distance. The confidence intervals are essential for use of inferred distance information by the Greedy Path-Merging method (ref. 16).

If a sequence fragment matches the reference sequence above the threshold T, a match is declared and the inferred distance is reported. In the following, the inventor considers methods for inferring particular types of positional information about fragments based on matches of fragments against the reference sequence.

B. Inferring Fragment Localization

The first type of information that is inferred is the information that a fragment is localized within a subregion. In the prior art, this information is obtained exclusively through the clone-by-clone shotgun method by tracking the clone of origin for each fragment. A method for inferring localization of fragments by comparison to second nucleic acid is illustrated in FIG. 1. The first step in the process is to identify a set of fragments that are known to fall within a subregion of the first nucleic acid. For example, such set of fragments may be the fragments obtained from the same BAC clone of insert size 200 Kb. In the second step the fragments are compared against the reference nucleic acid. In the third step a position ("subregion center") of the reference nucleic acid is calculated by averaging positions where fragments match reference nucleic acid. Center of subregion (101) is a position in the reference nucleic acid. Radius (102) is then defined as half the estimated size of the subregion from the original nucleic acid (in case of a BAC from our example, the radius is 100 Kb). Finally, if a previously unlocalized fragment (103) from the first nucleic acid matches reference sequence within the radius of the center of subregion, it is inferred that it also falls within the subregion of the original nucleic acid (in our example, it would be inferred that the fragment also falls within the BAC).

C. Inferring Fragment Overlap

The second type of information that is inferred is the information about the overlap of two fragments. In the prior art this information cannot be obtained with certainty based on sequence similarity of fragments due to the potential presence of repetitive elements and repeat-induced similarities between fragments. A method for inferring overlap of fragments by comparison to second nucleic acid is illustrated in FIG. 2. In the first step, overlap of two fragments (201 and 202) from the original nucleic acid is inferred if they match in an overlapping fashion a region (203) in the reference nucleic acid (204). Such overlap is considered "confirmed". In the second step, two fragments whose overlap is confirmed may be replaced by a single fragment that results from the assembly of the two fragments.

D. Inferring Distance Between Fragments

The third type of information that is inferred is the information about the distance between two fragments. In the prior art this information is obtained through the sequencing of mate pairs and involves significant additional experimental and logistic effort. A method for inferring fragment distances by comparison to second nucleic acid is illustrated in FIG. 3. Distance between two fragments (301 and 302) from the original nucleic acid is inferred as the distance (303) between unique matches (304 and 305) of the two fragments in the reference sequence. If a match of a fragment is not unique, the strongest match is considered, but only in case the strongest match is significantly better (say, at least 5% better) that the second-strongest match for the same fragment. If any of the fragments does not have a unique match, or an acceptable strongest match, distance between fragments is not inferred.

The inferred distance is accompanied by a confidence interval (plus or minus three standard deviations from the estimated distance). The standard deviations are estimated empirically based on a control set of fragments of known distance in the first nucleic acid. The deviation is calculated based on the observed differences of the inferred distance from the true known distance under an assumption that the differences are normally distributed.

E. Detecting False Overlaps

The fourth type of information that is inferred is the information about false fragment overlaps. Such overlaps are typically induced by the presence of a previously unknown repetitive element that occurs at both the end of one fragment and at the beginning of another fragment. False overlaps cause significant assembly problems and significant effort has been directed toward at least partially alleviating the problem. Present invention utilizes the information present in the reference nucleic acid in order to alleviate the problem of false overlaps.

A method for detecting false overlaps is illustrated in FIG. 4. First, the fragments are tested for the presence of known repetitive elements. If the presence of a known repeat is established and if the similarity between fragments can be explained by the presence of a repetitive element, false overlap is considered detected; otherwise, move to the next step. In the next step, the matches of the two fragments against the reference sequence are considered. If the two fragments both match the reference sequence at a distance (404) that precludes overlap, false overlap is detected; otherwise, no action is taken.

F. Detecting New Repetitive Elements

The fifth type of inferred information are the sequences of previously unknown repetitive elements. This information is obtained as a by-product of the method for detecting false overlaps, as is illustrated in FIG. 4. In the first step, presence of a repetitive element is inferred by detecting the situation where the end sequence (403) of one fragment matches the beginning sequence (402) of the other fragment but the fragments are inferred to occur at a distance by comparison against the reference nucleic acid. In the second step, check whether the match of the fragments to the reference sequence is complete or only partial (with non-matching overhangs). If the match is partial, the non-matching parts of the fragments comprise the sequence of a repetitive element. If the match is complete, then the region of similarity between the two fragments is detected as the sequence of a repetitive element.

G. Inferring BAC Overlaps

The sixth type of information that is inferred is the information about the overlap of two subregions from the first nucleic acid (say BACs). In the prior art this information requires costly fingerprinting experiments and cannot be obtained with certainty (ref 20,21). A method for inferring overlap of subregions by comparison to second nucleic acid is illustrated in FIG. 6. In the first step, overlap of two subregions (601 and 602) from the original nucleic acid is inferred if sequence fragments derived from both subregions match in an interleaved or overlapping fashion a region (603) in the reference nucleic acid (604). The minimum requirement for interleaving is that a match of a fragment from first subregion occurs between matches of two fragments from the second subregion or vice versa, or, alternatively, that two fragments, each representing a separate subregion, match the reference nucleic acid in an overlapping fashion. In the second step, two subregions whose overlap is inferred at high confidence are replaced by a single subregion that results from the assembly of the two subregions.

H. Sequence Matching Implementation

One should note that fragments are typically matched in both the direct orientation and as reverse complements. Fragments may be matched either at the nucleic acid sequence level or as translated amino acid sequence. The amino acid sequence may be translated in three different frames and in direct and reverse-complement orientations of the nucleic acid, thus resulting in six translated amino acid sequences per single nucleotide sequence fragment. A variety of well-known sequence matching and alignment methods (as described in (ref 10)) may be used for the purpose of finding matches between sequences of fragments and the sequence of the second nucleic acid, including BLAST, FASTA, and dynamic-programming based methods such as global alignment and Smith-Waterman alignment. In particular, the widely used FASTA method (ref. 26) is useful, especially for amino acid sequence comparisons, because of its speed and its sensitive alignment of longer fragments.

While a reference nucleic acid sequence, such as a complete genomic sequence, is an ideal reference for the disclosed method, scaffolds are used instead in situations where they are available and where the complete reference sequence is not available. Scaffold comparison is performed by the method described in (ref. 18).

While the different types of positional information outlined above can be obtained from an individual reference sequence, multiple reference sequences or scaffolds, or combinations thereof are used whenever available. If multiple references are used, distances inferred from individual references are combined pooled by calculating a mean value. Standard deviations and confidence intervals are combined by applying well-known statistical techniques for combining multiple measurements of the same quantity in the presence of measurement error.

I. Utilization of the Positional Information in the Assembly Process

The inventor here describes how is the positional information used in the context of a large genome sequencing project. The block diagram in FIG. 5 describes the information flow in the disclosed method. The portion of the diagram to the left of the dotted line in FIG. 5 illustrates the methods of inferring positional information while the portion of the diagram to the right illustrates the hierarchical OLC sequence assembly process.

It should be recognized that smaller-scale sequencing projects consist only of a subset of steps outlined in the diagram in FIG. 5. For example, BAC-level sequencing would not require the Global Assembly step (507). Nevertheless, the inventor here describes the most difficult process in order to employ all the kinds of inferred positional information that described in sections B, C, D, E, F, and G.

The portion of the diagram in FIG. 5 to the left of the dotted line illustrates the methods of inferring positional information based on reference sequence (501), The six grayed blocks correspond to the six methods for inferring positional information disclosed in sections B (block 510), C (540), D (520), E (550), F (530), and G (560). Localization information (511) is inferred (510) as described in section B and the newly localized fragments are simply added to the appropriate BACs (512) for processing by the screener/overlapper (504) and the BAC-level assembler (505). Distance information (521) is inferred (520) as described in section D and the newly inferred fragment distances are simply added to the appropriate mate pair distance information (522) for processing by the screener/overlapper (504) and the BAC-level assembler (505). The information about new repeats (531) is inferred (530) as described in section F and the newly inferred repeat sequences are simply added to the database of known repeat sequences (533) for processing by the screener/overlapper (504). The information about confirmed overlaps (541) is inferred (540) as described in section C and made available for use by the screener/overlapper (504), and the confirmed overlaps that come from a particular BAC are used to assemble the shorter fragments into a longer fragment and thus increase the phase (from 0 to 1) of individual BACs (512). The information about repeat-induced overlaps (551) is inferred (550) as described in section E and made available for use by the screener/overlapper (504) and the BAC-level assembler (505). The information about subregion (BAC) overlaps (561) is inferred (560) as described in section G, is simply combined with the overlap information obtained by physical mapping (562), and then made available for use by the genome-level assembler (507).

The portion of the diagram in FIG. 5 to the right of the dotted line illustrates a hierarchical OLC sequence assembly process that utilizes previously described components used in the assembly of genomes of Drosophila (ref. 8) and Human (ref 20,21). BAC shotgun sequencing (502) and whole-genome shotgun sequencing are performed using standard methods (ref. 20,21).

The Screener/Overlapper (504) performs the two-step function of first screening sequence fragments for the presence of repetitive elements and, second, detecting overlaps between fragments for use in the subsequent layout stage. If the available hardware and processor speed are the bottleneck in a genome scale project, an appropriate Screener/Overlapper for genome-scale projects has been described in (ref 8), otherwise, the use of BLAST searches for both repeat screening in the Screener step and overlap searches in the Overlapper steps is appropriate. An appropriate setting for the Screener (ref. 8) is "hard screen" and an appropriate threshold for detecting overlaps by the Overlapper is fewer than 6% differences in 40 bp unmasked (unscreened) sequence, as described in (ref. 8).

The inferred information (541, 551) is combined with the information produced by the Screener/Overlapper using the following rule: Each inferred overlap (541) is simply added to the set of overlaps detected by the overlapper. Each detected false overlap (551) is looked up in the list of overlaps produced by the overlapper and, if found, is deleted from the list.

An appropriate method for the BAC-level Assembler (505) step is the Greedy PathMerging method, as disclosed in (ref 16). The Greedy Path-Merging method smoothly integrates the shotgun fragment information at the BAC level with the genome-level shotgun information, including mate pair distances. One of the features of the Greedy Path-Merging method is that it breaks spurious assemblies at the BAC level ("bactigs"). The only straightforward modification required of the Greedy Path-Merging method is that it should break the bactigs that contain false repeat-induced overlaps detected by comparisons against the reference sequence (551). Otherwise, the method should be applied as described in (ref. 16). The breaking of erroneous assemblies due to repeat-induced overlaps (551) should significantly improve the overall quality of assemblies at the BAC level.

Global Assembler method merges BAC-level assemblies into a global assembly guided by a physical BAC map (562). Note that the inferred BAC overlap information (561) is simply added to the physical map information (562) prior to the processing by the Global Assembler. Thus, no changes to the Genome-level Assembler are necessary in order to accommodate the inferred positional information. Depending on the degree of fragment coverage and other factors, the output (508) of the Genome-level Assembler consists either of a complete sequence or of a number of sequence scaffolds, each scaffold consisting of a number of mutually oriented sequence contigs.

An appropriate embodiment of the Genome-level Assembler (507) is the four-step method outlined in FIG. 6 of (ref 20). The GigAssembler method (ref 24) performs this set of four steps but it also uses additional information such as messenger RNAs and ESTs. In case such additional information is available, GigAssembler is an appropriate embodiment.

Note that in cases where the second (reference) nucleic acid and the first (to be assembled) nucleic acid share significant similarity, such as, for example, the similarity between the genomic DNA of humans and chimpanzees or between the genomic DNA of different organisms within the same species, the inferred positional information may completely substitute the information ordinarily obtained by other means. In other words, a method illustrated in the diagram in FIG. 5 may in this case be modified by eliminating blocks (502), (533) and (562) and by replacing "BAC" by "subregion" and by omitting the phrase "and mate pair distances" from block (522) and the method would still work. In other words, with the help of the reference sequence a true "genome level shotgun" method where neither clone-by-clone sequencing nor mate pair information is tracked would be feasible.

Finally, while the diagram in FIG. 5 illustrates a complete genome-level sequencing method, parts of the diagram may also be performed independently. For example, in order to achieve BAC-level assembly one may omit the Genome-level assembly step (507). Indeed, if the fragment coverage is very high (say 15-fold) and if the great majority of BACs fed into (507) are Phase 3 (fully assembled sequence), the whole-genome level assembly problem becomes quite trivial.

J. Choice of Assembly Programs

It should be noted that the choice of assembly programs to be used in conjunction with the present invention depends on the circumstances of the particular application. Discussions of the advantages and disadvantages of particular methods abound in the cited literature (ref. 1,5,8,13,16,19,21,20,24). Published information needs to be taken into account when deciding which assembly method or a combination of methods is most appropriate for the particular application. The following is a practical guide for selecting the most appropriate method: if the sequence to be assembled does not exceed 3 Mb and redundancy of coverage exceeds 7×, then apply EULER method (ref. 19), otherwise, if the coverage is less than 7×, apply CAP3 (ref. 5). If the project is whole-genome sequencing of genomes significantly larger than 3 Mb, and if BAC-level shotgun is combined with whole genome shotgun including mate-pair information, apply Greedy Path-Merging method to improve BAC-level assembly (ref 16) and then apply the GigAssembler method (ref. 20,24) to combine BAC-level assemblies into a genome-scale assembly. Otherwise, if a whole-genome eshotgun approach is pursued and mate-pair information is available, apply the Whole Genome Assembly method (ref. 8,21).

In as much as the information inferred by the methods described in the present invention is identical in form to the information otherwise utilized by the assembly programs, the information inferred by the present invention is simply added to the other existing information to improve the assembly process. In one embodiment the inferred distance information is identical in form to the mate-pair information and is directly utilized by the Greedy Path Merging method (ref 16). In yet another embodiment, the inferred BAC localization is identical in form to the BAC localization inferred by the BAC-level shotgun method and is used directly in BAC-level assembly by CAP3 (ref 5) or the Greedy Path-Merging method (ref 16). In a further embodiment, the inferred information about fragment overlaps is used to replace two short fragments by a longer fragment obtained by merging the two short fragments and thus improve the performance of the EULER assembler by resolving "tangles" (ref 19). In a yet further embodiment, the inferred information about repeat-induced false overlaps is directly used in the Greedy Path-Merging method for breaking up erroneous bactigs (ref 16). In an even further embodiment, the inferred information about newly detected repeated sequence is used by the the Screener/Overlapper (ref. 8) in order to detect and tag repeat-induced overlaps prior to the layout stage of the assembly process. In a still further embodiment, the inferred information about BAC overlaps is added to the BAC overlap information obtained through restriction fingerprint analysis to improve the assembly produced by the GigAssembler method (ref 20,24).

It should be noted that different assembly programs utilize different subsets of the positional information that is inferred as described in the present invention. For example, EULER assembler does not utilize the mate pair or distance information (ref. 19). A practitioner with ordinary skill in the art should be able to competently decide which types of inferred information, as described in the present invention, are usable by the particular assembly program.p The accuracy of inferred information may vary. The inferred information is useful despite the fact that it is not perfect. The assembly programs currently in use tolerate certain level of error in the input and implement methods that in effect assemble sequence using preponderance of evidence.

It should be noted that in cases where the second (reference) nucleic acid and the first (to be assembled) nucleic acid share significant similarity, such as, for example, the similarity between the genomic DNA of humans and chimpanzees or between the genomic DNA of different organisms within the same species, the inferred positional information eliminates the need for information ordinarily obtained by other means. In one embodiment the inferred distance information eliminates the need for the mate-pair information and is directly utilized instead of the mate-pair information by the Greedy Path Merging method (ref 16), thus enabling whole-genome shotgun assembly without mate-pair information tracking. In yet another embodiment, the inferred subregional localization of fragments to subregions of size 10 Kb to 10 Mb eliminates the the BAC localization inferred by the BAC-level shotgun method and is used directly in subregion-level assembly by CAP3 (ref 5) or the Greedy Path-Merging method (ref 16), thus enabling whole-genome shotgun method without the need for BAC-level shotgun sequencing. In a still further embodiment, the inferred information about BAC overlaps eliminates the need for other BAC overlap information, thus enabling tiling-path construction and global assembly by the GigAssembler method without the step of restriction fingerprint analysis of individual BACs (ref. 20,24).

K. Improvements Achieved through Application of the Disclosed Method

From the point of view of sequence assembly, the effort saved through application of the disclosed method may be measured by the decrease in the number of fragment sequencing experiments that need to be performed for assembly of the sequence of the first nucleic acid. By applying the Lander-Waterman model (mathematical model establishing relationships between key variables in genome mapping) one can calculate that in the case of the mapping of genome of bacterium E. coli 20% of effort would be saved while in the case of the mapping of genome of yeast C. cerevisiae roughly 60% effort can be saved.

Lander-Waterman analysis does not apply to many higher eukaryotic genomes (such as human and mouse) due to presence of a large number of repetitive elements. Repetitive elements impede sequence assembly by causing sequence similarity between non-overlapping fragments. Such similarity may lead to assembly errors or to ambiguous (incomplete) assemblies. The method disclosed herein is uniquely suited to overcome the problem with repetitive elements due to the fact that it relies on inferred information about relative position of sequenced fragments, thus in effect creating "bridges" across the repeat-rich regions that are hard to assemble.

REFERENCES

The following references, to the extent that they provide exemplary procedural or other details supplementary to those set forth herein, are specifically incorporated herein by reference:

(ref. 1) J. K. Bonfield, K. F. Smith, and R. Staden. A new DNA sequence assembly program. *Nucleic Acids Research*, 23:4992-4999,1995.

(ref. 2) R Drmanac, I. Labat, I. Brukner, and R. Crkvenjakov. Sequencing of megabase plus DNA by hybridization: theory of the method. *Genomics*, 4:114-128, 1989.

(ref. 3) P. Green. Documentation for phrap. http:///bozeman-.mbt.washington.edu/phrap.docs/phrap.html, 1994.

(ref. 4) M. Grotschel, L. Lovasz, and A. Schrijver. *Geometric Algorithms and Combinatorial Optimization*. Springer-Verlag, 1993.

(ref. 5) X. Huang and A. Madan. CAP3 : A DNA sequence assembly program. *Genome Research*, 9:868-877, 1999.

(ref. 6) R. M. Idury and M. S. Waterman. A new algorithm for DNA sequence assembly. *Journal of Camputational Biology*, 2:291-306, 1995.

(ref. 7) Y. Lysov, V. Florent'ev, A. Khorlin, K. Khrapko, V. Shik, and A. Mirzabekov. DNA sequencing by hybridization with oligonucleotides. *Doklady Academy Nauk USSR*, 303:1508-1511, 1988.

(ref. 8) E. W Myers, G. G. Sutton, A. L. Delcher, I. M. Dew, D. P. Fasulo, M. J. Flanigan, S. A. Kravitz, C. M. Mobarry, K. H. Reinert, K. A. Remington, E. L. Anson, R. A. Bolanos, H. H. Chou, C. M. Jordan, A. L. Halpern, S. Lonardi, E. M Beasley, R. C. Brandon, L. Chen, P. J. Dunn, Z. Lai, Y Liang, D. R. Nusskern, M. Zhan, Q. Zhang, X. Zheng, G. M. Rubin, M. D. Adams, and J. C. Venter. A whole-genome assembly of Drosophila. *Science*, 287.2196-2204, 2000.

(ref. 9) J. Parkhill, M. Achtman, K. D. James, S. D. Bentley, C. Churcher, S. R. Klee, G. Morelli, D. Basham, D. Brown, T. Chillingworth, R. M. Davies, P. Davis, K. Devlin, T. Feltwell, N. Hamlin, S. Holroyd, K. Jagels, S. Leather, S. Moule, K. Mungall, M. A. Quail, M. A. Rajandream, K. M. Rutherford, M. Simmonds, J. Skelton, S. Whitehcad, B. G. Spratt, and B. G. Barrell. Complete DNA sequence of a serogroup A strain of *neisseria meningitidis* Z2491 *Nature*, 404:502-506, 2000.

(ref. 10) P. A. Pevzner. *Computational Molecular Biology: An Algorithmic Approach*. The MIT Pres, 2000.

(ref. 11) P. A. Pevzner. I-tuple DNA sequencing: computer analysis. *Journal of Biomolecular Structure and Dynamics*, 7:63-73, 1989.

(ref. 12) J. C. Roach, C. Boysen, K. Wang, and L. Hood. Pairwise end sequencing: a unified approach to genomic mapping and sequencing. *Genomics*, 26:345-353, 1995.

(ref. 13) G. Sutton, O. White, M. Adams, and A. Kerlavage. TIGR assembler. A new tool for assembling large shotgun sequencing projects. *Genome Science and Technology*, 1:919, 1995.

(ref. 14) H. Tettelin, D. Radune, S. Kasif, H. Khouri, and S. L. Salzberg. Optimized multiplex PCR: efficiently closing a whole-genome shotgun sequencing project. *Genomics*, 62:500-507, 1999.

(ref. 15) J. Weber and G. Myers. Whole genome shotgun sequencing. *Genome Research*, 7:401-409, 1997.

(ref. 16) D. H. Huson, K. Reinert, G. Myers. The greedy path-merging algorithm for sequence assembly. *Proceedings of the Fifth Annual International Conference on Computational Biology*, T. Lengauer, D. Sankoff, S. Istrail, P. Pevzner, M. Waterman, editors, 157-163, Association for Computing Machinery, New York, N.Y., 2001.

(ref. 17) J. Kececioglu, J. Yu. Separating repeats in DNA sequence assembly. *Proceedings of the Fifth Annual International Conference on Computational Biology*, T. Lengauer, D. Sankoff, S. Istrail, P. Pevzner, M. Waterman, editors, 176-183, Association for Computing Machinery, New York, N.Y., 2001.

(ref. 18) G. Myers. Comparing sequence scaffolds. *Proceedings of the Fifth Annual International Conference on Computational Biology*, T. Lengauer, D. Sankoff, S. Istrail, P. Pevzner, M. Waterman, editors, 224-230, Association for Computing Machinery, New York, N.Y., 2001.

(ref. 19) P. A. Pevzner, H. Tang, M. S. Waterman. A new approach to fragment assembly in DNA sequencing. *Proceedings of the Fifth Annual International Conference on Computational Biology*, T. Lengauer, D. Sankoff, S. Istrail, P. Pevzner, M. Waterman, editors, 256-267, Association for Computing Machinery, New York, N.Y., 2001.

(ref. 20) International Human Genome Sequencing Consortium. Initial sequencing and analysis of the human genome. *Nature,* 409:860-921, 2001.

(ref. 21) J. C. Venter et al., The sequence of the human genome. *Science,* 291:1304-1351, 2001.

(ref. 22) A. Edwards et al., Automated DNA sequencing of the human HPRT locus. *Genomics,* 6:593-608, 1990.

(ref. 23) Rat Genome Spurs an Unusual Partnership. *Science.* 291: 1872, 2001.

(ref. 24) W. J. Kent and D. Haussler. GigAssembler: an algorithm for the initial assembly of the human working draft. Technical Report UCSC-CRL-00-17 (University of California at Santa Cruz, Santa Cruz, Calif., 2001).

(ref. 25) F. S. Collins and V. A. McKusick, *Journal of American Medical Association,* 285:540-544, 2001.

(ref. 26) D. J. Lipman and W. R. Pearson. Rapid and sensitive protein similarity searches. *Science,* 227:1435-1441, 1985.

What is claimed is:

1. A method for predicting a sequence of at least a first nucleic acid comprising the steps of:
    (a) identifying by a sequencing method a first plurality of subsequences from said first nucleic acid;
    (b) comparing by a computer program stored in a computer the first plurality of subsequences with at least a second nucleic acid sequence;
    (c) identifying by said computer program stored in a computer for each subsequence from said first plurality a matching subsequence within said second nucleic acid sequence, the matching subsequences occurring at a distance from each other within said second nucleic acid sequence;
    (d) determining relative position of each of said matching subsequences within second nucleic acid sequence, said relative position of matching subsequences comprising a number indicating distance between said matching subsequences within second nucleic acid sequence; and
    (e) assembling, using a computer program stored in a computer, said first plurality of subsequences into a sequence assembly by simultaneously
        (i) maximizing overlap between said first plurality of subsequences; and
        (ii) minimizing the difference between the relative position of said first plurality of subsequences in the sequence assembly and the relative position of their corresponding said matching subsequences within second nucleic acid sequence;
    whereby the sequence assembly predicts the sequence of at least said first nucleic acid.

2. The method of claim 1, wherein said number indicates distance of between two thousand and one hundred million basepairs.

3. The method of claim 1, wherein said relative position of matching subsequences comprises a pair of numbers indicating a range of distances between said matching subsequences within second nucleic acid sequence, one number from said pair of numbers indicating the low end of the range and the other number from said pair of numbers indicating the high end of the range.

4. The method of claim 1, wherein said relative position of matching subsequences further comprises one number indicating confidence of distance information.

5. The method of claim 1, wherein said relative position of matching subsequences comprises a binary indicator of relative DNA strand orientation of said matching subsequences within second nucleic acid sequence.

6. The method of claim 1, wherein said first plurality of subsequences is identified by hybridization of said first nucleic acid with a set of oligonucleotide probes.

7. The method of claim 1, wherein said first plurality of subsequences is identified by electrophoretic sequencing reactions.

8. The method of claim 1, wherein said first plurality of subsequences is identified by dideoxy sequencing reactions.

9. The method of claim 1, wherein said matching subsequences are identified by performing a DNA sequence similarity search between the first plurality of subsequences and said second nucleic acid.

* * * * *